US006434408B1

(12) United States Patent
Heckel

(10) Patent No.: US 6,434,408 B1
(45) Date of Patent: Aug. 13, 2002

(54) PULSE OXIMETRY METHOD AND SYSTEM WITH IMPROVED MOTION CORRECTION

(75) Inventor: Donald W. Heckel, Brighton, CO (US)

(73) Assignee: Datex-Ohmeda, Inc., Madison, WI (US)

(*) Notice: Subject to any disclaimer, the term of this patent is extended or adjusted under 35 U.S.C. 154(b) by 0 days.

(21) Appl. No.: 09/675,596

(22) Filed: Sep. 29, 2000

(51) Int. Cl.[7] ................................................. A61B 5/00

(52) U.S. Cl. ...................................................... 600/336

(58) Field of Search ................................ 600/310, 323, 600/330, 336

(56) References Cited

U.S. PATENT DOCUMENTS 4,960,126 A * 10/1990 Conlon et al. ............... 600/336
5,190,038 A * 3/1993 Polson et al. ................ 600/330

* cited by examiner

Primary Examiner—Eric F. Winakur
(74) Attorney, Agent, or Firm—Marsh Fischmann & Breyfogle LLP

(57) ABSTRACT

A pulse oximetry method and system for improved motion correction is disclosed. The method/system provides for the use of a detector output signal to obtain a different plurality of differential absorption data sets in corresponding relation to each of a succession of measurement, wherein each of the data sets includes differential absorption values for light of a first wavelength and light of a second wavelength. The data sets are processed to obtain a relative motion estimate value for each measurement. When the relative motion estimate value for a given measurement falls within a predetermined range (i.e., corresponding with clinical motion), a corresponding blood analyte indicator value is adjusted in a predetermined manner, wherein the corresponding adjusted blood analyte indicator is employable to obtain at least one blood analyte concentration value. In one embodiment, blood analyte indicator values may be readily multiplied by a predetermined adjustment factor (i.e., when clinical motion is identified). The relative motion estimate value for a given measurement Sep. 27, 2000 may be obtained by conducting a principal component analysis of the corresponding plurality of data sets relative to a corresponding best fit function therefor to obtain corresponding variance values $V_1$, $V_2$. The variance value $V_1$, and/or $V_2$ for a given current measurement may be employed to obtain a current motion estimate value. The current motion estimate value and the relative motion estimate value obtained for a prior low motion measurement (i.e., for which no adjustment was necessary) may be used to compute the relative motion estimate value for the current measurement. The variance values $V_1$ and/or $V_2$ are also employable to compute an ongoing, updated motion probability factor, wherein such factor may be used to adjust relative motion estimates values in instances of rapid tissue perfusion changes.

45 Claims, 6 Drawing Sheets

PULSE OXIMETRY METHOD AND SYSTEM WITH IMPROVED MOTION CORRECTION

FIELD OF THE INVENTION

The present invention generally pertains to patient monitoring using photoplethysmographic devices to generate blood analyte information. More particularly, the invention is directed to an efficient and effective approach for reducing the undesired effects of motion-contaminated data in pulse oximetry devices.

BACKGROUND OF THE INVENTION

In the field of photoplethysmography light signals corresponding with two or more different centered wavelengths may be employed to non-invasively determine various blood analyte concentrations. By way of primary example, blood oxygen saturation ($SpO_2$) levels of a patient's arterial blood are monitored in pulse oximeters by measuring the absorption of oxyhemoglobin and reduced hemoglobin using red and infrared light signals. The measured absorption data allows for the calculation of the relative concentrations of reduced hemoglobin and oxyhemoglobin, and therefore $SpO_2$ levels, since reduced hemoglobin absorbs more light than oxyhemoglobin in the red band and oxyhemoglobin absorbs more light than reduced hemoglobin in the infrared band, and since the absorption relationship of the two analytes in the red and infrared bands is known.

To obtain absorption data, pulse oximeters comprise a probe that is releaseably attached to a patient's appendage (e.g., finger, ear lobe or the nasal septum). The probe directs red and infrared light signals through the appendage, or tissue-under-test. The light signals are provided by one or more sources which are typically disposed in the probe. A portion of the light signals is absorbed by the tissue-under-test and the intensity of the light transmitted through the tissue-under-test is detected, usually by at least one detector that may be also located in the probe. The intensity of an output signal from the detector(s) is utilized to compute $SpO_2$ levels, most typically via a processor located in a patient monitor interconnected to the probe.

As will be appreciated, pulse oximeters rely on the time-varying absorption of light by a tissue-under-test as it is supplied with pulsating arterial blood. The tissue-under-test may contain a number of non-pulsatile light absorbers, including capillary and venous blood, as well as muscle, connective tissue and bone. Consequently, detector output signals typically contain a large non-pulsatile, or DC, component, and a relatively small pulsatile, or AC, component. It is the small pulsatile, AC component that provides the time-varying absorption information utilized to compute arterial $SpO_2$ levels.

In this regard, the red and infrared signal portions of pulse oximeter detector output signals each comprise corresponding large DC and relatively small AC components. The red and infrared signal portions have an exponential relationship to their respective incident intensities at the detector(s). As such, the argument of the red and infrared signal portions have a linear relationship and such portions can be filtered and processed to obtain a ratio of processed red and infrared signal components (e.g., comprising their corresponding AC and DC components), from which the concentration of oxyhemoglobin and reduced hemoglobin in the arterial blood may be determined. See, e.g., U.S. Pat. No. 5,934,277. By utilizing additional light signals at different corresponding centered wavelengths it is also known that carboxyhemoglobin and methemoglobin concentrations can be determined. See, e.g., U.S. Pat. No. 5,842,979.

As noted, the pulsatile, AC component of a pulse oximeter detector output signal is relatively small compared to the non-pulsatile DC component. Consequently, the accuracy of analyte measurements can be severely impacted by small amounts of noise. Of particular concern here is noise that contaminates absorption data as a result of undesired variations in the path length of light signals as they pass through the tissue-under-test. Such variations are most typically caused by patient movement of the appendage to which a pulse oximetry probe is attached.

A number of different approaches have been utilized to reduce the deleterious effects of patient motion in pulse oximeters. For example, pulse oximeter probes have been developed to enhance the physical interface between the probe and tissue-under-test, including the development of various clamp type probe configurations and secure wrap-type probe configurations. Further, numerous approaches have been developed for addressing motion contaminated data through data processing techniques. While such processing techniques have achieved a degree of success, they often entail extensive signal processing requirements, thereby contributing to increased device complexity and componentry costs.

SUMMARY OF THE INVENTION

In view of the foregoing, a general objective of the present invention is to provide an improved method and system for addressing motion correction in pulse oximeters.

More particularly, primary objectives of the present invention are to provide for motion correction in pulse oximeters in a manner that is effective and that reduces complexity and component requirements relative to data processing-intensive prior art devices.

The above objectives and additional advantages are realized in the present invention. In this regard, the present inventor has recognized that patient motion can be generally classified into a limited number of motion ranges, or bands, for motion correction purposes. A first type of motion, which may be referred to as "low motion", corresponds with a range of patient motions that do not have a significant effect on the absorption data comprising a detector output signal. A second type of motion, which may be referred to as "clinical motion", corresponds with patient motion that primarily affects the AC component of a detector output signal in a relatively predictable manner across a range of motion severity. For such clinical motion, the present inventor has further recognized that a predetermined adjustment factor may be effectively utilized to correct blood analyte measurements, thereby avoiding complex data processing requirements.

The above-noted recognitions provide the basis for a number of improvements to pulse oximetry systems in which a detector provides an output signal indicative of light absorption of a tissue-under-test at each of a plurality of different centered light wavelengths (e.g. centered at red and infrared wavelengths) and which utilize the output signal to obtain blood analyte indicator values for each of a succession of measurements (e.g., periodic measurements corresponding with partially overlapping or non-overlapping measurement data) during a patient monitoring procedure. The inventive method/system provides for the utilization of the detector output signal to obtain a corresponding relative motion estimate value for each measurement. For such purposes, the detector output signal may be processed to yield a different plurality of differential absorption data sets for each measurement, wherein each data set includes a first differential absorption value for light at the first wavelength $dA_{\lambda_1}$ (e.g., infrared light) and a corresponding-in-time second differential absorption value for light at the second wavelength $dA_{\lambda_2}$ (e.g., infrared light). As will be appreciated, the plurality of data sets corresponding with each given measurement are obtained over an associated time period, wherein each successive measurement employs a different successive plurality of data sets, and wherein the data sets employed for successive measurements may or may not partially overlap. By way of primary example, the differential absorption data sets may be obtained via derivative or logarithmic processing of a series of data samples that correspond with a detected infrared portion of a detector output signal and a corresponding-in-time series of data samples that correspond with a detected red light portion of the detector output signal.

For each of the measurements the method/system provides for a determination of whether or not the corresponding relative motion estimate value (RMEV) is within a first predetermined range (e.g. corresponding with a predetermined range of clinical motion), wherein for measurements having a corresponding RMEV within the first predetermined range the corresponding blood analyte indicator value (BAIV) may be adjusted in a predetermined manner. Such adjustment may provide for the use of a predetermined adjustment factor (e.g., determined empirically). For measurements indicating clinical motion, the adjusted BAIVs may be utilized to obtain a more accurate measure of blood analyte concentration (e.g. the relative concentration of oxygenated hemoglobin and reduced hemoglobin for $SpO_2$ level determination). As will be appreciated, one or more clinical motion bands, with corresponding predetermined RMEV ranges and adjustment factors, may be employed in accordance with the present invention.

As noted, the present inventor has recognized that for a certain range of patient motion, referred to as low motion herein, the impact of the motion on blood analyte measurements is negligible. As such, the inventive method/system may further provide for a determination as to whether the relative motion estimate value (RMEV) for each of the plurality of measurements is within a second predetermined range (e.g., corresponding with low motion). For each measurement having a corresponding RMEV within the second predetermined range, the corresponding blood analyte indicator value may be employed without adjustment to obtain blood analyte concentration values.

The RMEV obtained with respect to each given measurement period may entail the computation of a best-fit function for the corresponding plurality of differential absorption data sets. By way of example, the best-fit function may be defined as the slope value of a regression line (e.g. determined via least squares or linear regression processing) for a "plot" of the differential absorption values for light at the first wavelength $dA_{\lambda_1}$ versus the corresponding-in-time differential absorption values for light at the second wavelength $dA_{\lambda_2}$. As may be appreciated, the best fit function obtained with respect to each measurement period may also be utilized as the corresponding BAIV, e.g., the "best-fit RRatio" value as taught in U.S. Pat. No. 5,954,277. Alternatively, a first plurality of differential absorption data sets may be computed for use in the computation of the RMEV; and a second plurality of differential absorption data sets may be separately computed for use in the determination of the BAIVs as taught in a co-pending U.S. patent application entitled "Method And Apparatus For Determining Pulse Oximetry Differential Values", filed contemporaneous herewith and hereby incorporated by reference.

In conjunction with the obtainment of a best fit function for each given measurement, the inventive method/system may further provide for the performance of a statistical analysis of the corresponding plurality of a differential absorption data sets in relation to the best fit function to obtain at least one statistical variance value indicative of a degree of any associated motion, wherein the statistical variance value(s) may be utilized to compute the corresponding RMEV. In primary embodiments, the statistical analysis may comprise a principal component analysis (PCA). That is, for each measurement the plurality of differential absorption data sets (i.e., each comprising corresponding-in-time $dA_{\lambda_1}$ and $dA_{\lambda_2}$ values) may be statistically analyzed in relation to the corresponding best fit function to obtain at least one of a first principal component variance value ($V_1$) and a second principal component variance value ($V_2$). In this regard, $V_1$ may be computed to represent an amplitude-based statistical variance, while $V_2$ may be computed to represent a scatter-based statistical variance. The relative motion estimate value for a given measurement may be determined utilizing at least one, and preferably both, of the corresponding first and second principal component variance values $V_1$ and/or $V_2$.

More particularly, in one embodiment, for each given one of a plurality of measurements the inventive method/system may provide for the calculation of a corresponding current motion estimate value (CMEV) utilizing the corresponding $V_1$ and $V_2$ values, and the identification of a reference motion value (RMV), wherein the corresponding relative motion estimate value (RMEV) is computed utilizing both the CMEV and RMV. In one arrangement, the CMEV for each given measurement may be calculated as follows:

$$CMEV = V_1 * V_2$$

In turn, the RMEV for each given measurement may be calculated as a ratio of the corresponding CMEV and RMV, e.g.:

$$RMEV = \frac{CMEV}{RMV}.$$

The RMV may be established on an ongoing, updated basis to be equal to the RMEV that corresponds with the lowest amount of motion (e.g., the lowest RMEV) determined with respect to any prior measurement (e.g. preferably corresponding low motion) for a given patient monitoring procedure (i.e., a "low motion reference"). At the outset of a given measurement procedure and/or where there is otherwise no prior low motion reference basis for establishing an RMV, the RMV for the given measurement may be established as follows:

$$RMV = \frac{V_1}{V_2} CMEV * K,$$

where $V_1$, $V_2$ and CMEV are as determined with respect to the given current measurement and K is a constant.

As indicated, for measurements having an RMEV within a first predetermined range, i.e., corresponding with clinical motion, a predetermined adjustment factor (PAF) may be utilized to adjust the corresponding blood analyte indicator value (BAIV) for use in blood analyte concentration computations. Such adjustment may entail the ready application, e.g., by multiplication, of the PAF to the computed BAIV. In this regard, the PAF may be empirically set via statistical analysis of clinical motion-affected absorption data and corresponding-in-time, non-motion-affected absorption data obtained via testing of test subject control groups.

In one embodiment, for measurements having computed BAIVs that exceed a predetermined threshold value, the PAF may be scaled in relation to the predetermined threshold value. For example, in applications where each BAIV is defined by the slope value of a regression line, the PAF for a given BAIV may be scaled follows:

$$Scaled\ PAF = 1 - \left[\left[\frac{BAIV - A}{B - A}\right] * (1 - PAF)\right],$$

wherein A and B are predetermined constants, and wherein no scaling occurs when:

$$BAIV > B,$$

and wherein PAF may be set to 1 when:

$$BAIV < A.$$

In arrangements where the BAIVs are defined by regression line slope values as noted above, the PAF may be preferably set between about 0.5 and 0.85, and most preferably between about 0.6 and 0.75 (e.g., about 0.6875 in one arrangement where A=0.9455 and B=0.65).

In additional aspects of the present invention, the inventive method/system may further comprise additional features to insure appropriate motion correction where there has been a rapid, significant change in the perfusion of a tissue-under-test. By way of example, such variations may occur as a result of the application of a tourniquet or blood pressure cuff, or as a result of inadvertent contact with a patient "pressure point" (e.g., that cuts off arterial blood flow to the tissue under test). To address such instances the inventive method/system may provide for the ongoing, periodic determination of a motion probability factor (MPF), wherein if the MPF exceeds a predetermined threshold the reference motion value (RMV) may be adjusted using the MPF.

The MPF may be computed via a statistical analysis of the plurality of differential absorption data sets corresponding with each of all given one of a series of measurements in relation to a corresponding best fit function computed therefore, wherein at least one statistical variance value may be obtained for use as an MPF value. More particular, the MPF may be computed utilizing of $V_2$ and/or $V_1$ values computed with respect to each current a series of measurements and computed with respect to one or more prior measurements. In one approach, an average $V_2$ value is determined in relation to each given measurement, wherein each average $V_2$ value is calculated by averaging the sum of the $V_2$ value for a given period and the $V_2$ values for a predetermined number of immediately precedent measurements. Then, an MPF for each given measurement may be computed utilizing a comparison, or ratio, between the average $V_2$ value computed for the current measurement and the lowest average $V_2$ value computed with respect to any prior measurement (e.g., current average $V_2$ value/lowest average $V_2$ value).

In one arrangement, the system/method may be established so that an RMV adjustment may be made when (i) a predetermined number of successive, non-low motion measurements have occurred, and (ii) the motion probability factor (MPF) for the current measurement period is determined to exceed a predetermined threshold. When the predetermined threshold is exceeded, the RMV may be adjusted as follows:

$$adjusted\ RMV = CMEV + (CMEV - RMV)(MPF)K,$$

wherein CMEV and MPF are as determined with respect to the current measurement and K is a constant.

In addition to the implementation of one or more clinical motion ranges and a low motion range, embodiments of the present invention may also address patient motion that exceeds clinical motion and may be referred to as "severe motion". In such embodiments, the present invention accommodates an approach wherein no blood analyte measurement values are output to a user during "severe motion" (e.g., when measurements have corresponding RMEVs outside of the predetermined clinical motion and low motion RMEV ranges).

Alternatively, to address severe motion embodiments may be employed which provide for the use and adjustment of a previously determined blood analyte indicator value (BAIV). For example, the BAIV for the most recent non-severe motion measurement may be adjusted by an adjustment factor for use in blood analyte concentration computations. The adjustment factor may be based upon tracking of the DC components of the detector output signal portion (s) corresponding with the detected light at the first and/or second centered-wavelength(s) signals. That is, the adjustment factor may be computed as the ratio between such DC component(s) measurement, and such DC components corresponding with at least a current, given severe motion measurement (i.e. a measurement obtained utilizing data obtained during severe motion.

In this regard, in one embodiment the detector output signal may be utilized to obtain moving average values of total tissue absorption of the AC and DC signal components corresponding with each of the first and second light signals ($MAV_{\lambda 1}$, $MAV_{\lambda 2}$), e.g., for red and infrared signal components, wherein such moving average values are computed for a predetermined precedent time interval in conjunction with each measurement (e.g., an average for a predetermined number of measurements that include the current measurement and a number of prior measurements). In the event severe motion is detected with respect to a given measurement period, e.g. when the corresponding RMEV is not within a predetermined low motion range or any predetermined clinical motion range, the BAIV corresponding with the most recent, non-severe motion measurement may be adjusted by a DC tracking factor (DCTF), as follows:

$$DCTF = \frac{\frac{MAV_{\lambda 2}}{MAV_{\lambda 1}}\ for\ most\ recent\ pre-severe\ motion\ measurement}{\frac{MAV_{\lambda 2}}{MAV_{\lambda 1}}\ for\ current\ severe-motion\ measurement} K,$$

wherein K is a constant; then:

$$adjusted\ BAIV = BAIV * DCTF.$$

The adjusted BAIV may then be employed for enhanced blood analyte determinations for the given severe motion measurement. As may be appreciated, this inventive aspect may be advantageously utilized in a number of arrangements, including embodiments where no clinical motion bands are defined/employed for motion correction purposes. For example, this feature may be separately utilized with the system/method disclosed in PCT Publication No. WO 98/04903, PCT Application No. PCT/CH97/00282, hereby incorporated by reference.

Additional aspects and other combinations of the present invention will be apparent to those skilled in the art upon review of the further description that follows.

DETAILED DESCRIPTION

Figure 1:
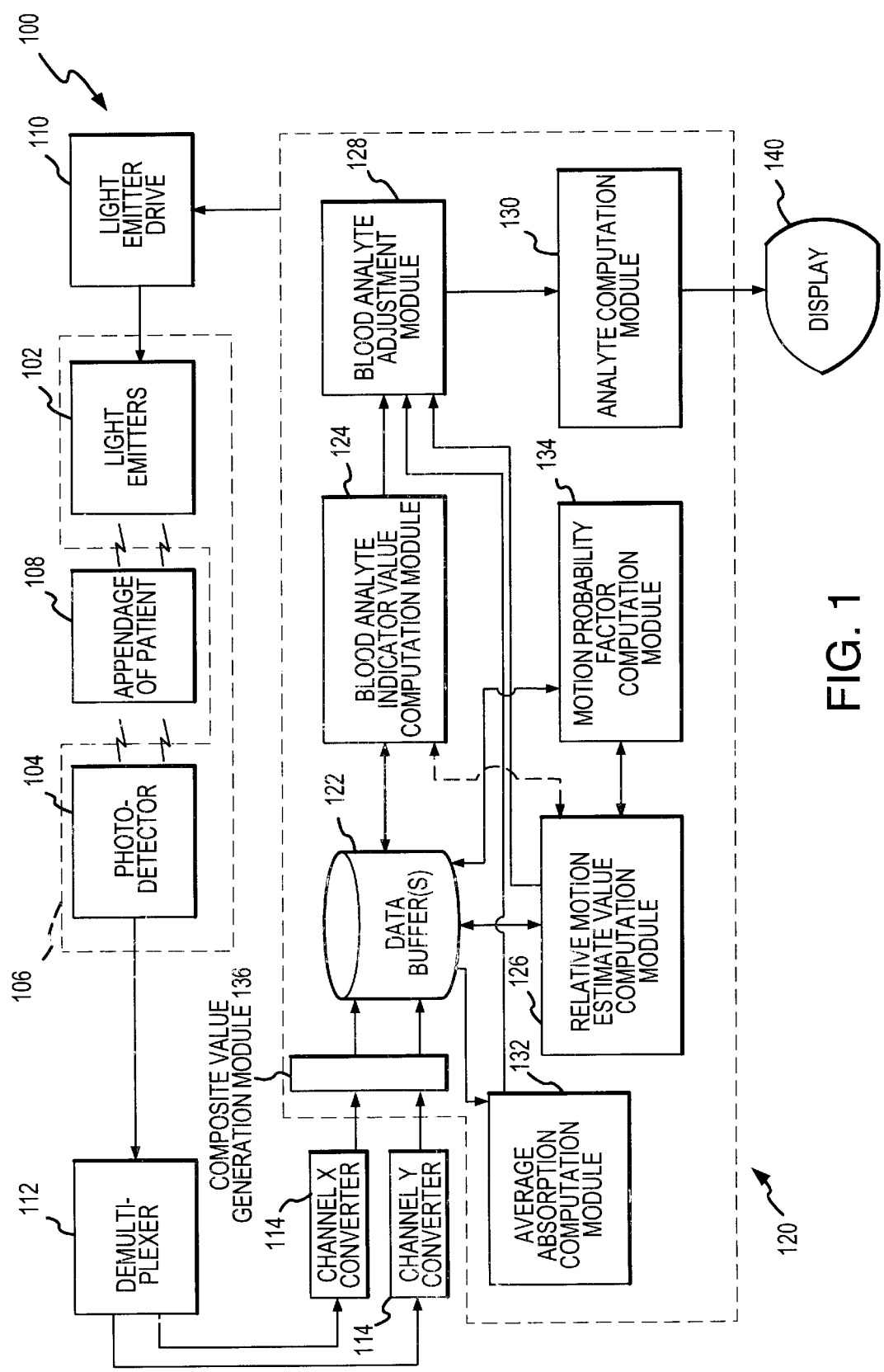
FIG. 1 is a block diagram of one embodiment of a system for implementation of the present invention.
Figure 2:
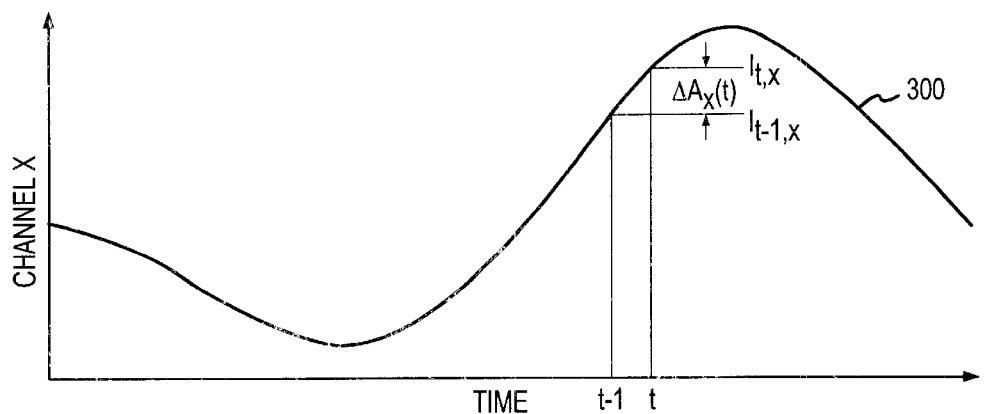
FIG. 2 illustrates an exemplary pulse waveform received on channel X of the FIG. 1 embodiment.

Referring to FIG. 1, a pulse oximeter system 100 according to one embodiment of the present invention is shown. Included in the system 100 are two light emitters 102 for radiating red light signals and infrared light signals and a photodetectors 104. By way of example, the light emitters 102 may be light emitting diodes (LEDs) or laser diodes.

The emitters 102 and photodetector(s) 104 may be incorporated into a probe 106 adapted for removable attachment to an appendage 100 of a patient, such as a finger, earlobe, nasal septum, or other tissue, during a monitoring procedure. In use, the probe 106 directs the light signals generated by the light emitters 102 onto one side of the appendage 100. Photodetector(s) 104 is positioned on the opposite side of the appendage 108 to monitor the intensity of light that is transmitted through the tissue and produce an output signal responsive thereto. As may be appreciated, the red and infrared emitters 102 may be driven by a drive 110 within interconnected processor unit 120 so that the output signal of detector(s) 104 is multiplexed according to a predetermined scheme (e.g., time-division multiplexed, frequency division multiplexed, code-division multiplexed, etc.).

In turn, a demultiplexer 112 may be provided to separate the detector output signal into infrared and red signal portions on two processing channels, e.g. channels X and Y, respectfully. Signal converters 114 may be provided in each channel X, Y, with current-to-voltage amplifiers, analog-to-digital converters, and other componentry for digitizing the red and infrared signal portions for processing by processor unit 120. As will be appreciated, demultiplexer 112 may be provided in a hardware form or implemented in software downstream of converters 114 at processor unit 120.

In accordance with the described system embodiment 100, the processor unit 120 is provided for automatic motion correction in an effective and efficient manner. For such purposes, processor unit 120 may comprise a front-end module 136 that receives digitized AC and DC detector signal values on both channels X and Y and generates a series of composite infrared and composite red signal values, respectively (e.g., 30 values each per sec.). Such processing may entail the use of preset AC gain and DC gain values, preset A/D ground values, and preset light emitter drive levels to normalize the AC and DC values. Processor unit 120 may further comprise one or more data storage buffer(s) 122 to temporarily store data sets comprising the composite red and infrared signal values received from module 136, as well as additional values computed by computation modules of processor unit 120. In the later regard, the data stored in buffer(s) 122 may be accessed for use by a number of preprogrammed computation modules comprising the processor unit 120.

In particular, a blood analyte indicator value computation module 124 may access the composite infrared and red data signal values in buffer(s) 122 to compute differential infrared and red absorption data sets (e.g., 30 sets/sec.) from which blood analyte indicator values may be determined for each of a succession of measurements (e.g., every ½ sec.) during patient monitoring. Each blood analyte indicator value (BAIV) may be defined to corresponded with a best fit function determined for a plurality of data sets (e.g., 64 sets) utilized for a given measurement. Computed BAIVs may be at least temporarily stored at buffer(s) 122 for use in accordance with the described embodiment.

A relative motion estimate value computation module 126 may also access the composite infrared and red data signal values in buffer(s) 122 to compute differential absorption data sets (e.g., 30 sets sec.) from which relative motion estimate values may be successively determined for each measurement (e.g., every ½ sec.) during patient monitoring. In this regard, module 126 may utilize a plurality of differential absorption data sets (e.g., 64 sets) for a given measurement to determine a best fit function and corresponding motion variance valves $V_1$, $V_2$ via a principal component analysis (PCA). The motion variance values $V_1$, $V_2$ corresponding with each given measurement period provide an indication of the degree of patient motion occurring during the period associated with data sets employed for such measurement. Module 126 may utilize the $V_1$ and/or $V_2$ value(s) to compute a current motion estimate value (CMEV) for each measurement, and to establish a reference motion value (RMV). The CMEV and RMV may be employed in module 126 to compute a reference motion estimate value (RMEV) for each measurement. Computed RMEV and RMV values may be at least temporarily stored at buffer(s) 122.

As indicated by FIG. 1, the blood analyte indicator values computed at module 124 and relative motion estimate values computed at module 126 may be provided to an adjustment module 128 that may adjust, or correct, the blood analyte indicator value (BAIV) for each given measurement when the corresponding relative motion estimate value (RMEV) is within a first predetermined motion range corresponding with clinical motion. When the RMEV corresponding with a given measurement period falls within a second predetermined range corresponding with low patient motion (e.g., non-overlapping with the first range), the BAIV for that measurement will not be adjusted by module 128. As will be appreciated, the adjusted and unadjusted BAIVs corresponding with successive measurements may be provided to an analyte computation module 130 for computation of blood analyte concentrations. The computed concentration levels may be output to user, e.g., via a display 140 provided at a patient monitor. The monitor may also house the emitter drive 110, signal converters 114, processor unit 120, and in alternate embodiments demultiplexer 112, emitters 102 and/or detector(s) 104.

Referring further to FIG. 1, processor unit 120 may also include a motion probability factor computation module 134 that may interface with module 126 and buffer(s) 122 to obtain computed RMEV and PCA variance values $V_1$ and/or $V_2$. Module 134 may employ such values to compute a motion probability factor (MPF) on an ongoing updated basis (e.g. corresponding with each measurement). In turn, the MPF may be utilized to adjust the RMV utilized in module 126 to compute the RMEVs.

Finally, the processor 120 may further include an average absorption computation module 132 which may access the composite infrared and red values in buffer(s) 122 to compute average total infrared and red absorption values for predetermined intervals(e.g., corresponding with a predetermined number of successive measurements), in corresponding relation to each given measurement. As will be further described, such average absorption values may be utilized in certain embodiments in connection with the correction of blood analyte indicator values utilized for measurements having corresponding relative motion estimate values that fall within a severe patient motion range.

Figure 3:
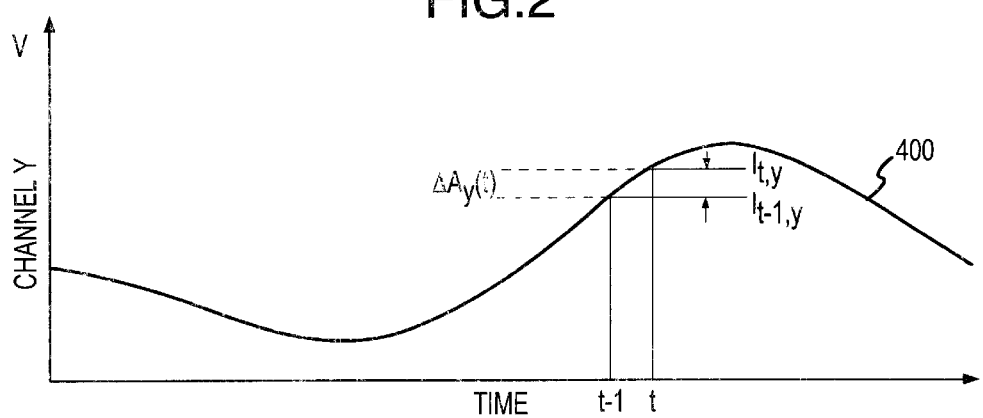
FIG. 3 illustrates an exemplary pulse waveform received on channel Y of the FIG. 1 embodiment.
Figure 4:
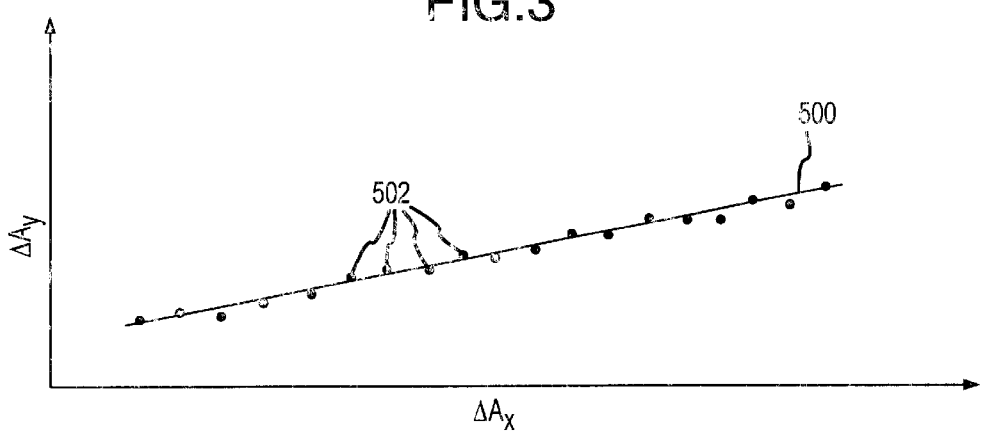
FIG. 4 is plot of differential absorption data set values $dA_x$, $dA_y$ obtained via channels X and Y of the FIG. 1 embodiment, and corresponding with low patient motion.

As noted, modules 124 and/or 126 may access data buffer(s) 122 to obtain composite infrared and red values from which differential absorption data sets may be computed with respect to each given measurement. For purposes of describing such differential absorption data sets, reference is now made to FIGS. 3 and 4 which illustrate pulse waveforms 300 and 400, corresponding with the intensity of the digitized, corresponding-in-time composite infrared and red signal values generated at module 136 of processor unit 120 for channels X and Y, respectively. By way of example, derivative processing of successive data samples on channel X and on channel Y may be approximated to obtain differential absorption valves $dA_x$ and $dA_y$, as follows:

$$dA_x \cong DA_x = (I_{t,x} - I_{t-1,x})/[(I_{t,x} + I_{t-1,x})/2], \text{ and}$$

$$dA_y \cong DA_y = (I_{t,y} - I_{t-1,y})/[(I_{t,y} + I_{t-1,y})/2].$$

Alternatively, the differential absorption values may be obtained by calculating differences between the logarithm values of successive infrared and successive red composite signal values.

In one embodiment, the computation of differential absorption valves $dA_x$, $dA_y$ at modules 124 and 126 may be conducted separately, wherein module 126 employs processing techniques taught, in a copending U.S. Patent Application entitled "Method and Apparatus for Determining Pulse Oximetry Differential Values", filed contemporaneous herewith and hereby incorporated by reference. Alternatively, modules 124 and 126 may utilize the same $dA_x$, $dA_y$ values, with best fit functions computed for each measurement utilized both modules 124 and 126.

Figure 5:
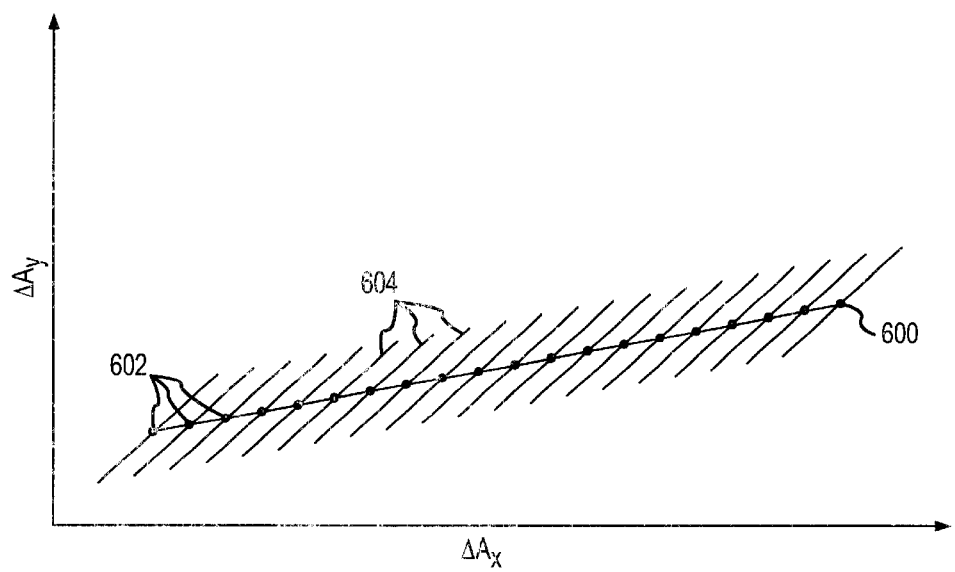
FIG. 5 is a plot illustrating exemplary 45-degree bias lines for data sets affected by motion.

To further describe such best fit functions, reference is now made to FIG. 5. In FIG. 5, a plurality of differential absorption data sets $dA_x$, $dA_y$ that correspond with low motion are presented. That is, each data point represents a plot of a differential absorption value $dA_x$ versus a corresponding-in-time differential absorption value $dA_y$. A linear regression analysis has been performed on the data set to determine a regression line 500, or best fit function, that best fits the data sets. The slope value of line 500 represents a normalized ratio of $dA_x$, and $dA_y$ for the corresponding measurement and may be used in a known manner to determine an $SpO_2$ level.

Figure 6:
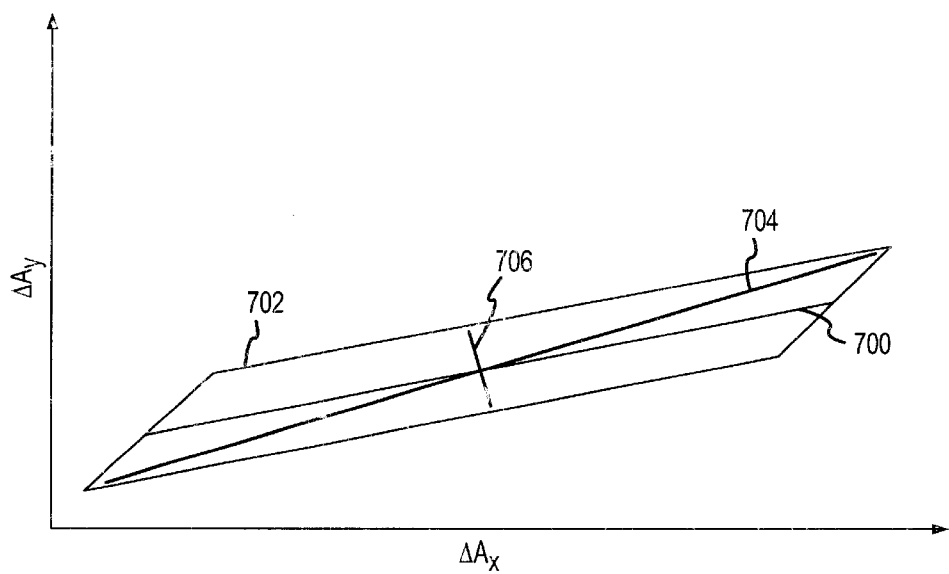
FIG. 6 is a plot illustrating first and second principal components in a principal component analysis (PCA) of a set of differential absorption values.

As noted, module 126 of processor unit 120 computes a relative motion estimate value (RMEV) for each measurement. Each such value may be determined utilizing a computed best fit function for the corresponding differential absorption data sets. For purposes of further explanation, reference is now made to FIG. 6 which illustrates in plot form an important observation of how motion may affect the data corresponding with a given measurement period. In particular, it has been found that for motion within a clinical motion range the effects upon corresponding differential absorption values $dA_x$ and $dA_y$ may be substantially the same. Thus a plotted data point affected by motion may be biased, e.g., along a 45-degree angle line. The regression line 600 shows where plotted data points should lie if no motion is present. The lines slanted at 45-degree 604 represent how data points 602 may be displaced when the differential absorption values $dA_x$, and $dA_y$ are affected by clinical motion.

Figure 7:
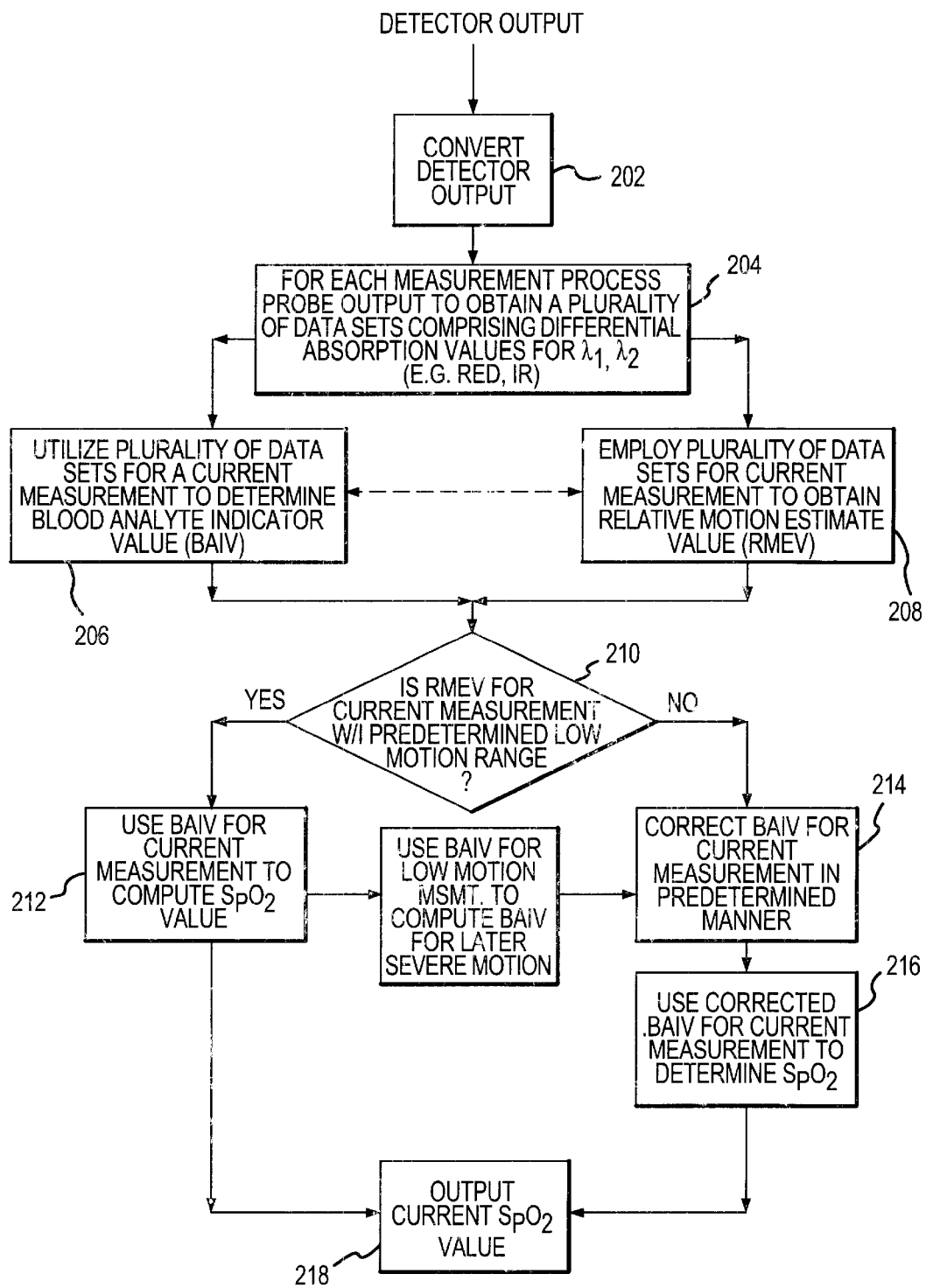
FIG. 7 is a flow diagram of one embodiment of methodology comprising the present invention.

In one embodiment, the operation of module 126 is based upon the observation described above in relation to FIG. 6. More particularly, module 126 may utilize a best fit function, or regression line, for each given measurement to perform a principal component analysis (PCA) of the corresponding differential absorption data sets, wherein variance values $V_1$ and $V_2$ may be determined. FIG. 7 graphically illustrates the results of a PCA performed on a plurality of data sets, having a best fit line 700, to obtain corresponding $V_1$ and $V_2$ values. The distribution box 702 of the data points (not shown individually) may be described using first and second principal component vectors and derived from the PCA. Each of the principal component vectors accounts for a different amount of variation among the data points. The first principal component vector describes the cluster of data points disposed along a longitudinal axis 704. The second principal component vector corresponds with an axis 706 extending perpendicular to the first axis 704. With vectors describing variations among the set of data points relative to axes 704, 706, any number of algorithms may be used to estimate an amount of motion associated therewith.

For example, in one approach, let x denote the dA for channel X and y denote the dA for channel Y. The calculations may be based on a buffer of n pairs of data $(x_i, y_i)$. The calculations may be based on the five following summations:

$$S_1 = \sum_{i=1}^{n} x_i,$$

$$S_2 = \sum_{i=1}^{n} x_i^2,$$

$$S_3 = \sum_{i=1}^{n} y_i,$$

$$S_4 = \sum_{i=1}^{n} y_i^2,$$

and $$S_5 = \sum_{i=1}^{n} x_i y_i.$$

These are then used to calculate $$u = S_2 - \frac{S_1^2}{n},$$

$$w = S_4 - \frac{S_3^2}{n},$$

and $$p = S_5 - \frac{S_1 S_3}{n}.$$

The regression slope may then calculated to be $$\beta = \frac{w - u + \sqrt{(u-w)^2 + 4 \cdot p^2}}{2 \cdot p}.$$

The correlation coefficient between x and y is $$r = \frac{p}{\sqrt{u \cdot w}}.$$

The variation of the points along the regression line is the variance $V_1$ associated with the first principal component, and the variation of the perpendicular distance to this line is the variance $V_2$ associated with the second principal component. As previously noted, these values are useful in evaluating the presence and degree of motion.

The variance $V_1$ of the first principal component may be expressed as:

$$V_1 = \frac{u + \beta^2 w + 2\beta p}{1 + \beta^2},$$

and the variance $V_2$ of the second principal component may be expressed as:

$$V_2 = \frac{w + \beta^2 u - 2\beta p}{1 + \beta^2}.$$

The utilization of $V_1$ and $V_2$ values in conjunction with various modules comprising processor 120 will be further described below.

Figure 8:
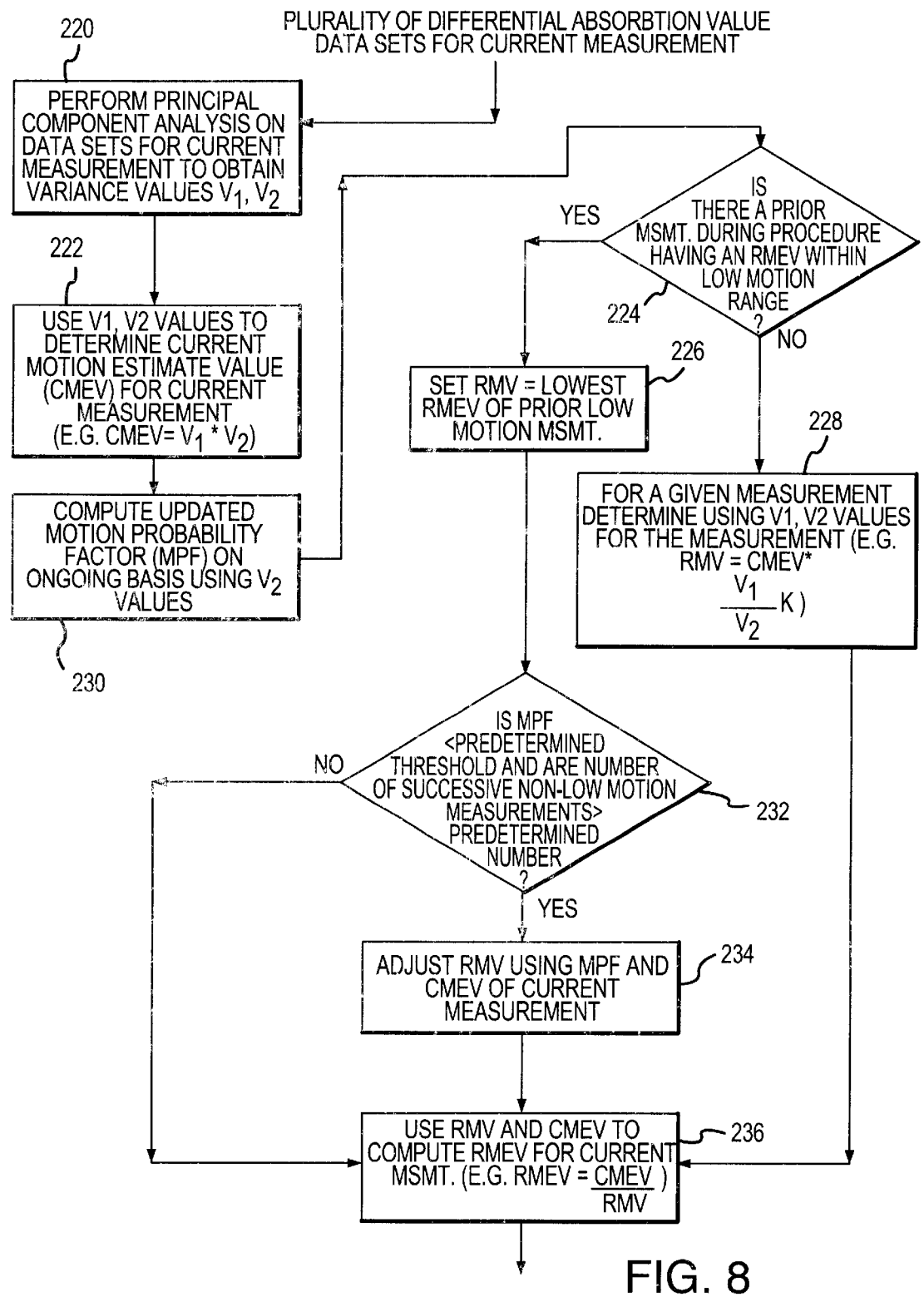
FIG. 8 is a flow diagram of one approach for obtaining relative motion estimate values (RMEVs) in the embodiment of FIG. 7.
Figure 9:
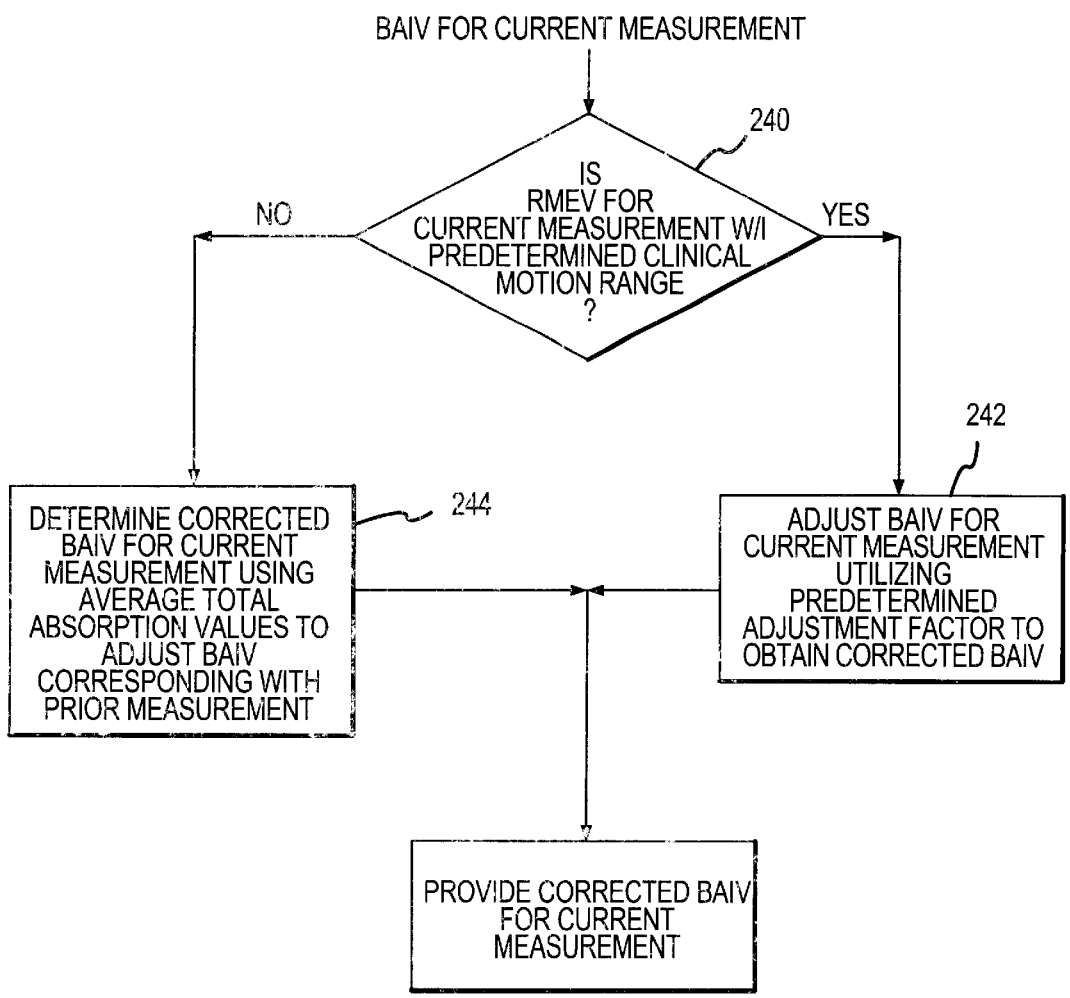
FIG. 9 is a flow diagram of one approach for correcting blood analyte indicator values (BAIVs) in the embodiment of FIG. 7.

In this regard, FIGS. 7–9 illustrate process steps in the operation of one implementation of the present invention. As shown in FIG. 7, a detector output current signal may be initially converted (step 202) into a digital form and composite red and infrared values may be obtained from the converted signal. Following signal conversion, the red and infrared detector output signal portions may be processed to obtain at least a first plurality of differential absorption data sets for each successive measurement (step 204). A plurality of the data sets may be employed to obtain a corresponding blood analyte indicator value (BAIV) for each measurement (step 206), e.g., a best fit function as described above. Correspondingly, a plurality of data sets may be utilized to obtain a relative motion estimate value (RMEV) for each measurement (step 208).

In one embodiment, the RMEV for each measurement may be determined according to the method steps shown in FIG. 8. As illustrated therein, a principal component analysis (PCA) may be conducted on the data sets corresponding with each current measurement relative to a corresponding computed best fit function to obtain variance values $V_1$, $V_2$ (step 220). In turn, a current motion estimate value CMEV may be determined with respect to each current measurement (step 222), as follows:

$$CMEV = V_1 * V_2.$$

As further shown in FIG. 8, a reference motion value (RMV) may also be established on an ongoing updated basis. More particularly, the RMV may be established to be equal to the lowest RMEV for any prior measurement having an RMEV in the low motion range (steps 224, 226). If no prior low motion measurement is available (step 224), the RMV for a given measurement may be determined as follows (step 228):

$$RMV = \frac{V_1}{V_2} CMEV\ K,$$

where $V_1$, $V_2$ and CMEV are determined in the manner described above for the current measurement, and K is predetermined constant.

Pursuant to the determination of $V_1$ and $V_2$ values, the illustrated process may also provide for the computation of a motion probability factor (MPF) on an ongoing, updated basis utilizing the $V_2$ measurement values (step 230). More particularly, an average $V_2$ value may be computed for each measurement by averaging the $V_2$ value for the given measurement together with the $V_2$ determined with respect to predetermined number of immediately precedent measurements. In turn, the MPF at a given measurement may be determined by comparing the average $V_2$ value for the current measurement with the lowest average $V_2$ value computed with respect to any prior measurement (e.g., by computing a ratio value therebetween).

The MPF may be advantageously utilized to adjust the RMV (e.g., as determined in step 226) to address rapid changes in the perfusion of the tissue-under-test. In the illustrated process embodiment, such adjustment may be made in the event that the MPF exceeds a predetermined threshold after a predetermined number of successive non-low motion measurements (step 232). In the event an adjustment to an RMV is to be made, the MPF and RMV may be utilized together with the CMEV for the current measurement to make such adjustment (step 234). More particularly, such adjustment may be made as follows:

$$\Delta\ Adjustment = (CMEV - RMV) * MPF,$$

and, if i$\Delta$ Adjustment < $CMEV*A$, then:

$$\Delta\ Adjustment = CMEV*A,$$

and, $$RMV = CMEV - \Delta\ Adjustment,$$

wherein A is a predetermined constant.

As illustrated in FIG. 8, the CMEVs for each of the measurements, together with 15 the RMV (as set in Step 226, Step 228, or as adjusted in Step 234) may be utilized to compute the RMV for each measurement (step 236). In the illustrated embodiment, the RMV values may be determined as follows:

$$RMEV = \frac{CMEV}{RMV},$$

wherein CMEV corresponds with the current measurement.

Returning now to FIG. 7, the illustrated process further provides for a determination of whether or not the RMEV for each given measurement is within a predetermined low motion range (step 210). As previously described, the predetermined low motion range may be set so that no adjustment of the blood analyte indicator value computed at step 206 is necessary (step 212). In the event that the RMEV for a given measurement does not fall within the low motion range, the corresponding blood analyte indicator may be corrected (step 214). For such purposes, reference will now be made to FIG. 9, which illustrates one embodiment for correction.

In particular, and as shown in FIG. 9, an initial determination may be made as to whether the relative motion estimate value (RMEV) for a given measurement is within a predetermined clinical motion range (step 240). In the event clinical motion is identified, the corresponding blood analyte indicator value (BAIV) may be adjusted in a predetermined manner. In one embodiment a best fit function, or slope value, computed for the given measurement may be simply adjusted by a predetermined factor to obtain an adjusted BAIV (step 242). By way of example, in one embodiment if a given BAIV is greater than a predetermined constant B the BAIV may be multiplied by a predetermined adjustment factor (PAF) to obtain the adjusted BAIV. On the other hand, if the BAIV is less than the predetermined constant B yet greater than a predetermined constant A, the PAF may be scaled as follows:

$$Scaled\ AF = 1 - \left(\frac{BAIV - A}{B - A}\right) * (1 - PAF).$$

In the event that the BAIV for a given measurement is less than the predetermined value A no adjustment of the BAIV is conducted.

In the event that a given relative motion estimate value (RMEV) is not within the second predetermined range, a number of options are possible. In one embodiment, a corrected blood analyte indicator may be obtained utilizing a BAIV for a prior low motion measurement (step 244), as adjusted by DC tracking component (step 244). More particularly, the BAIV computed for the most recent non-severe motion measurement preceding a given severe motion period may be utilized in the computation of a BAIV. In particular, the pre-severe motion measurement BAIV may be multiplied by a DC tracking factor (DCTF) to obtain a BAIV for the severe motion measurement. The DCTF may be computed as follows:

$$DCTF = \frac{\frac{MAV_{\lambda 2}}{MAV_{\lambda 1}}\ \text{for most recent pre-severe motion measurement}}{\frac{MAV_{\lambda 2}}{MAV_{\lambda 1}}\ \text{for current measurement}} K,$$

Wherein $MAV_{\lambda 1}$, $MAV_{\lambda 2}$ values are average total absorption values for the infrared and red portions of the detector output signal, respectively, as computed for the pre-severe motion measurement and for the current severe motion measurement, and K is a predetermined constant. To compute $MAV_{\lambda 1}$ $MAV_{\lambda 2}$ the light absorption values (i.e., DC plus AC components) for the infrared and red portions, respectively, of the detector output signal may be averaged for a predetermined number of successive measurements.

Returning now to FIG. 7, the illustrated embodiment finally provides for the use of blood analyte indicators for each of the measurement periods, as either adjusted or unadjusted, to compute a blood analyte concentration (step 212 and 216). By way of example, $SpO_2$ levels may be computed in a manner as taught in U.S. Pat. No. 5,934,277. In turn, the computed $SpO_2$ values may be output to a display 140 as previously noted (step 218).

The embodiment described above is for exemplary purposes only and is not intended to limit the scope of the present invention. Various adaptations, modifications and extensions of the described system/method will be apparent to those skilled in the art and are intended to be within the scope of the invention as defined by the claims which follow.

What is claimed is:

1. A method for use in a pulse oximetry system which provides a detector output indicative of light absorption by a tissue-under-test at each of a plurality of different light wavelengths, comprising:

utilizing said detector output to (i.) compute blood analyte indicator values for each of a plurality of measurements, and (ii.) obtain a corresponding relative motion estimate value for each of said plurality of measurements; and, determining whether the corresponding relative motion estimate value for each of said plurality of measurements is within a first predetermined range, wherein for at least one of said plurality of measurements having a corresponding relative motion estimate value within the first predetermined range the corresponding blood analyte indicator value is adjusted utilizing a predetermined adjustment factor that is empirically determined, and wherein said adjusted blood analyte indicator value is employable to obtain a blood analyte concentration value.

2. A method as recited in claim 1, wherein for said at least one of said plurality of measurements having a corresponding relative motion estimate value within the first predetermined range said predetermined adjustment manner includes:

adjusting the corresponding blood analyte indicator value utilizing a predetermined adjustment factor.

3. A method as recited in claim 2, wherein said adjusting step includes:

multiplying the corresponding blood analyte indicator value by said predetermined adjustment factor.

4. A method as recited in claim 3, wherein said adjusting step further includes:

comparing the corresponding blood analyte indicator value to a predetermined threshold value, wherein said predetermined adjustment factor is scaled when said blood analyte indicator value exceeds said predetermined threshold value.

5. A method as recited in claim 3, wherein said predetermined adjustment factor is set to a value between about 0.5 and 0.85.

6. A method as recited in claim 1, said utilizing step including:

processing said detector output to obtain a different plurality of data sets corresponding with each of said plurality of measurements, each of said plurality of data sets comprising a first differential absorption value for light at a first wavelength and a second differential absorption value for light at a second wavelength, wherein for each of said plurality of measurements a corresponding best fit function is computed for the corresponding plurality of data sets.

7. A method as cited in claim 6, wherein for each of said plurality of measurements said utilizing step further includes:
   performing a statistical analysis of the corresponding plurality of data sets in relation to the corresponding best fit function to obtain at least one statistical variance value indicative of a relative degree of patient motion; and,
   computing said corresponding relative motion estimate value using said corresponding at least one statistical variance value.

8. A method as cited in claim 6, wherein for each of said plurality of measurements said utilizing step further includes:
   performing a principal component analysis of the corresponding plurality of data sets in relation to the corresponding best fit function to obtain at least one of a first principal component variance value ($V_1$) and a second principal component variance value ($V_2$); and
   computing said corresponding relative motion estimate value using at least one of said corresponding first principal component variance value $V_1$ and said corresponding second principal component value $V_2$.

9. A method as recited in claim 8, wherein for each given one of said plurality of measurements said utilizing step further includes:
   calculating a corresponding current motion estimate value (CMEV) using at least one of said corresponding $V_1$ and $V_2$ values;
   establishing a reference motion value (RMV); and
   computing said corresponding relative motion estimate value (RMEV) using said corresponding CMEV and said RMV.

10. A method as recited in claim 9, wherein for each of said plurality of measurements:
    said CMEV is calculated as follows:

$$CMEV = V_1 * V_2;\ and,$$

said corresponding RMEV is determined as follows:

$$RMEV = \frac{CMEV}{RMEV}.$$

11. A method as recited in claim 10, wherein for at least one of said plurality of measurements said establishing step includes:

$$RMV = \frac{V_1}{V_2} CMEV^* K,$$

wherein $V_1$, $V_2$ and CMEV are as determined for said at least one of said plurality of measurements, and wherein K is a constant.

12. A method as recited in claim 9, wherein for at least one of said plurality of measurements said establishing step includes:
    setting the RMV equal to a lowest RMEV corresponding with a prior one of said plurality of measurements.

13. A method as recited in claim 12, wherein said establishing step further includes:

computing a motion probability factor (MPF) on an ongoing, updated basis utilizing at least one of said $V_1$ values and said $V_2$ values; and,
    using the MPF to adjust said RMV when the MPF exceeds a predetermined threshold.

14. A method as recited in claim 13, wherein said computing step further includes:
    determining an average $V_2$ value in relation to each given one of a series of measurements by averaging a sum of the $V_2$ value corresponding with the given measurement and the $V_2$ values corresponding with a predetermined number of prior measurements comprising said series, and,
    comparing the average $V_2$ value corresponding with each given one of the series of measurement periods with the lowest average $V_2$ value corresponding with any precedent one of said series of measurement periods to obtain a ratio therebetween, wherein said ratio is employable as said MPF.

15. A method as recited in claim 14, wherein in said using step said RMV is adjusted to an adjusted RMV as follows:

$$\text{adjusted } RMV = CMEV + (CMEV - RMV)(MPF)K,$$

wherein CMEV and MPF are as determined in relation to a given current measurement and K is a predetermined constant.

16. A method as recited in claim 1, further comprising:
    determining whether the relative motion estimate value corresponding with each of said plurality of measurements is within a second predetermined range, non-overlapping with said first predetermined range, wherein for each measurement having a corresponding relative motion estimate value within said second predetermined range the corresponding blood analyte indicator value is employable to obtain at least one blood analyte concentration value free from adjustment.

17. A method for use in pulse oximetry system which provides a detector output indicative of light absorption by tissue under test at each a plurality of different light wavelengths and which employs the detector output to compute blood analyte indicator value for each of the plurality of measurements, comprising:
    processing said detector output to obtain a plurality of data sets corresponding with each of said plurality of measurements, each of said plurality of data sets comprising a first differential absorption value for light at a first wavelength and a second differential absorption value light at a second wave wavelength, wherein for each of said plurality of measurements a corresponding best fit function is computed for the corresponding plurality of data sets;
    performing for each of said plurality of measurements a statistical analysis of the corresponding plurality of data sets in relation to the corresponding best fit function to obtain at least one statistical variance value;
    computing a relative motion estimate value for each of said plurality of measurements using said corresponding at least one statistical variance value; and,
    determining whether the corresponding relative motion estimate value for each of said plurality of said measurements is within a first predetermined range, wherein for at least one of a plurality of measurements having a corresponding relative motion estimate value within the first predetermined range, the corresponding blood analyte indicator value is adjusted utilizing a predetermined adjustment factor, and wherein the adjusted blood analyte indicator value is employable to obtain a blood analyte concentration value.

18. A method as provided in claim 16, wherein said blood analyte indicator values are each defined by a slope value of a regression line computed with respect to the corresponding plurality of data sets for a given measurement, and wherein the predetermined adjustment factor is set to a value between about 0.6 and 0.75.

19. A method as provided in claim 17, wherein for each of said plurality of measurements said performing step further includes:
conducting a principal component analysis of the corresponding plurality of data sets in relation to the corresponding best fit function to obtain at least one of a first principal component variance value ($V_1$) and a second principal component variance value ($V_2$); and,
computing said corresponding relative motion estimate value using at least one of said corresponding first principal component variance value ($V_1$) and said corresponding second principal component variance value ($V_2$).

20. A method as recited in claim 19, wherein said method further includes:
establishing a reference motion value (RMV); and, wherein for each given one of said plurality of measurements said computing step further includes:
calculating a corresponding current motion estimate value (CMEV) using at least one of said corresponding $V_1$ and $V_2$ values; and,
computing said corresponding relative motion estimate value (RMEV) using said corresponding CMEV and said corresponding RMEV.

21. A method as recited in claim 20, wherein said establishing step further includes:
computing a motion probability factor (MPF) on an updated basis utilizing at least one of said $V_1$ values and said $V_2$ values; and,
adjusting said RMV utilizing said MPF when said MPF exceeds a predetermined threshold.

22. A method for use in a pulse oximetry system which provides a detector output indicative of light absorption by a tissue-under-test at each of a plurality of different light wavelengths and which employs the detector output to compute blood analyte indicator values for each of a plurality of measurements, comprising:
utilizing said detector output to obtain a corresponding relative motion estimate value for each of said plurality of measurements by processing said detector output to obtain a different plurality of data sets corresponding with each of said plurality of measurements, each of said plurality of data sets comprising a first differential absorption value for light at a first wavelength and a second differential absorption value for light at a second wavelength, wherein for each of said plurality of measurements a corresponding best fit function is computed for the corresponding plurality of data sets; and,
determining whether the corresponding relative motion estimate value for each of said plurality of measurements is within a first predetermined range, wherein for at least one of said plurality of measurements having a corresponding relative motion estimate value within the first predetermined range the corresponding blood analyte indicator value is adjusted in a predetermined adjustment manner, and wherein said adjusted blood analyte indicator value is employable to obtain a blood analyte concentration value.

23. A method as cited in claim 22, wherein for each of said plurality of measurements said utilizing step further includes:
performing a statistical analysis of the corresponding plurality of data sets in relation to the corresponding best fit function to obtain at least one statistical variance value indicative of a relative degree of patient motion; and,
computing said corresponding relative motion estimate value using said corresponding at least one statistical variance value.

24. A method as cited in claim 22, wherein for each of said plurality of measurements said utilizing step further includes:
performing a principal component analysis of the corresponding plurality of data sets in relation to the corresponding best fit function to obtain at least one of a first principal component variance value ($V_1$) and a second principal component variance value ($V_2$); and,
computing said corresponding relative motion estimate value using at least one of said corresponding first principal component variance value $V_1$ and said corresponding second principal component value $V_2$.

25. A method as recited in claim 24, wherein for each given one of said plurality of measurements said utilizing step further includes:
calculating a corresponding current motion estimate value (CMEV) using at least one of said corresponding $V_1$ and $V_2$ values;
establishing a reference motion value (RMV); and,
computing said corresponding relative motion estimate value (RMEV) using said corresponding CMEV and said RMV.

26. A method as recited in claim 25, wherein for each of said plurality of measurements:
said CMEV is calculated as follows:

$$CMEV = V_1 * V_2; \text{ and,}$$

said corresponding RMEV is determined as follows:

$$RMEV = \frac{CMEV}{RMEV}.$$

27. A method as recited in claim 26, wherein for at least one of said plurality of measurements establishing step includes:

$$RMV = \frac{V_1}{V_2} CMEV^* K,$$

wherein $V_1$, $V_2$ and CMEV are as determined for said at least one of said plurality of measurements, and wherein K is a constant.

28. A method as recited in claim 25, wherein for at least one of said plurality of measurements said establishing step includes:
setting the RMV equal to a lowest RMEV corresponding with a prior one of said plurality of measurements.

29. A method as recited in claim 27, wherein said establishing step further includes:
computing a motion probability factor (MPF) on an ongoing, updated basis utilizing at least one of said $V_1$ values and said $V_2$ values; and,
using the MPF to adjust said RMV when the MPF exceeds a predetermined threshold.

30. A method as recited in claim 29, wherein said computing step further includes:
   determining an average $V_2$ value in relation to each given one of a series of measurements by averaging a sum of the $V_2$ value corresponding with the given measurement and the $V_2$ values corresponding with a predetermined number of prior measurements comprising said series, and,
   comparing the average $V_2$ value corresponding with each given one of the series of measurement periods with the lowest average $V_2$ value corresponding with any precedent one of said series of measurement periods to obtain a ratio therebetween, wherein said ratio is employable as said MPF.

31. A method as recited in claim 30, wherein in said using step said RMV is adjusted to an adjusted RMV as follows:

$$\text{adjusted } RMV = CMEV + (CMEV - RMV)(MPF)K,$$

wherein CMEV and MPF are as determined in relation to a given current measurement and K is a predetermined constant.

32. A method for use in a pulse oximetry system which provides a detector output indicative of light absorption by a tissue-under-test at each of a plurality of different light wavelengths, comprising:
   utilizing said detector output to obtain a corresponding relative motion estimate value for each of said plurality of measurements; and,
   determining:
      (i.) whether the corresponding relative motion estimate value for each of said plurality of measurements is within a first predetermined range, wherein for at least one of said plurality of measurements having a corresponding relative motion estimate value within the first predetermined range the corresponding blood analyte indicator value is adjusted in a predetermined manner, and wherein said adjusted blood analyte indicator value is employable to obtain a blood analyte concentration value; and,
      (ii.) whether the relative motion estimate value corresponding with each of said plurality of measurements is within a second predetermined range, non-overlapping with said first predetermined range, wherein for each measurement having a corresponding relative motion estimate value within said second predetermined range the corresponding blood analyte indicator value is employably to obtain at least one blood analyte concentration value free from adjustment.

33. A method as recited in claim 32, wherein for said at least one of said plurality of measurements having a corresponding relative motion estimate value within the first predetermined range said predetermined adjustment manner includes:
   adjusting the corresponding blood analyte indicator value utilizing a predetermined adjustment factor.

34. A method as recited in claim 33, wherein said adjusting step includes:
   multiplying the corresponding blood analyte indicator value by said predetermined adjustment factor.

35. A method as recited in claim 34, wherein said adjusting step further includes:
   comparing the corresponding blood analyte indicator value to a predetermined threshold value, wherein said predetermined adjustment factor is scaled when said blood analyte indicator value exceeds said predetermined threshold value.

36. A method as recited in claim 34, wherein said predetermined adjustment factor is set to a value between about 0.5 and 0.85.

37. A method as recited in claim 32, said utilizing step including:
   processing said detector output to obtain a different plurality of data sets corresponding with each of said plurality of measurements, each of said plurality of data sets comprising a first differential absorption value for light at a first wavelength and a second differential absorption value for light at a second wavelength, wherein for each of said plurality of measurements a corresponding best fit function is computed for the corresponding plurality of data sets.

38. A method as cited in claim 37, wherein for each of said plurality of measurements said utilizing step further includes:
   performing a statistical analysis of the corresponding plurality of data sets in relation to the corresponding best fit function to obtain at least one statistical variance value indicative of a relative degree of patient motion; and,
   computing said corresponding relative motion estimate value using said corresponding at least one statistical variance value.

39. A method for use in a pulse oximetry system which provides a detector output indicative of light absorption by a tissue-under-test at each of a plurality of different light wavelengths, comprising:
   utilizing said detector output to (i.) compute blood analyte indicator values for each of a plurality of measurements, and (ii.) obtain a corresponding relative motion estimate value for each of said plurality of measurements; and,
   determining whether the corresponding relative motion estimate value for each of said plurality of measurements is within a first predetermined range, wherein for at least one of said plurality of measurements having a corresponding relative motion estimate value within the first predetermined range the corresponding blood analyte indicator value is adjusted in a predetermined adjustment manner; and,
   separately employing, for each of said plurality of measurements, the corresponding blood analyte indicator value, as adjusted, to obtain a blood analyte concentration value.

40. A method as recited in claim 39, wherein for said at least one of said plurality of measurements having a corresponding relative motion estimate value within the first predetermined range said predetermined adjustment manner includes:
   adjusting the corresponding blood analyte indicator value utilizing a predetermined adjustment factor.

41. A method as recited in claim 40, wherein said adjusting step includes:
   multiplying the corresponding blood analyte indicator value by said predetermined adjustment factor.

42. A method as recited in claim 41, wherein said adjusting step further includes:
   comparing the corresponding blood analyte indicator value to a predetermined threshold value, wherein said predetermined adjustment factor is scaled when said blood analyte indicator value exceeds said predetermined threshold value.

43. A method as recited in claim 41, wherein said predetermined adjustment factor is set to a value between about 0.5 and 0.85.

44. A method as recited in claim 39, said utilizing step including:

processing said detector output to obtain a different plurality of data sets corresponding with each of said plurality of measurements, each of said plurality of data sets comprising a first differential absorption value for light at a first wavelength and a second differential absorption value for light at a second wavelength, wherein for each of said plurality of measurements a corresponding best fit function is computed for the corresponding plurality of data sets.

45. A method as cited in claim 44, wherein for each of said plurality of measurements said utilizing step further includes:

performing a statistical analysis of the corresponding plurality of data sets in relation to the corresponding best fit function to obtain at least one statistical variance value indicative of a relative degree of patient motion; and, computing said corresponding relative motion estimate value using said corresponding at least one statistical variance value.

\* \* \* \* \*

UNITED STATES PATENT AND TRADEMARK OFFICE
CERTIFICATE OF CORRECTION

PATENT NO. : 6,434,408 B1
DATED : August 13, 2002
INVENTOR(S) : Heckel

It is certified that error appears in the above-identified patent and that said Letters Patent is hereby corrected as shown below:

<u>Title page,</u>
Item [56], References Cited, U.S. PATENT DOCUMENTS, insert

| | | | | |
|---|---|---|---|---|
| -- | 5,490,505 | 2/1996 | Diab et al. | 128/633 |
| | 5,588,427 | 12/1996 | Tien | 128/633 |
| | 5,632,272 | 5/1997 | Diab et al. | 128/633 |
| | 5,662,105 | 9/1997 | Tien | 128/633 |
| | 5,685,299 | 11/1997 | Diab et al. | 128/630 |
| | 5,687,722 | 11/1997 | Tien et al. | 128/633 |
| | 5,766,127 | 6/1998 | Pologe et al. | 600/310 |
| | 5,796,785 | 6/1998 | Diab et al. | 600/364 |
| | 5,782,306 | 7/1998 | Serafin | 166/387 |
| | 5,842,979 | 12/1998 | Jarman | 600/322 |
| | 5,853,364 | 12/1998 | Baker, Jr., et al. | 600/300 |
| | 5,924,980 | 7/1999 | Coetzee | 600/300 |
| | 5,934,277 | 8/1999 | Mortz | 128/633 |
| | 6,036,642 | 3/2000 | Diab et al. | 600/364 |
| | 4,869,254 | 9/1989 | Stone et al. | 128/633 |
| | 4,955,379 | 9/1990 | Hall | 128/633 |
| | 5,078,136 | 1/1992 | Stone et al. | 128/633 |
| | 5,216,598 | 6/1993 | Branstetter et al. | 364/413.09 |
| | 5,278,627 | 1/1994 | Aoyagi et al. | 356/41 |
| | 5,497,796 | 3/1996 | Gratton et al. | 128/633 |
| | 6,151,107 | 11/2000 | Schollermann et al. | 356/41 |

EP   0 303 502 A1   12/1988 --.

Signed and Sealed this

Twelfth Day of November, 2002

Attest:

Attesting Officer

JAMES E. ROGAN
*Director of the United States Patent and Trademark Office*